United States Patent
Thompson (10) Patent No.: US 9,148,811 B2
(45) Date of Patent: *Sep. 29, 2015

(54) APPARATUS AND METHOD FOR DETECTING CO-CHANNELS SIGNALS

(71) Applicant: Anite Finland Oy, Oulu (FI)

(72) Inventor: Steven Thompson, Forest, VA (US)

(73) Assignee: Anite Finland OY, Oulu (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,205

(22) PCT Filed: Dec. 18, 2012

(86) PCT No.: PCT/FI2012/051262
§ 371 (c)(1),
(2) Date: Jun. 17, 2014

(87) PCT Pub. No.: WO2013/093195
PCT Pub. Date: Jun. 27, 2013

(65) Prior Publication Data
US 2014/0315507 A1    Oct. 23, 2014

Related U.S. Application Data

(63) Continuation of application No. 13/334,528, filed on Dec. 22, 2011, now Pat. No. 8,406,789.

(51) Int. Cl.
*H04M 1/00* (2006.01)
*H04W 24/08* (2009.01)
(Continued)

(52) U.S. Cl.
CPC ............. *H04W 24/08* (2013.01); *H04B 7/2125* (2013.01); *H04M 1/72519* (2013.01)

(58) Field of Classification Search
CPC . H04M 1/72519; H04W 8/246; H04W 24/00; H04W 56/00

USPC .......... 455/550.1, 418, 67.11, 456.1; 370/350
See application file for complete search history.

(56) References Cited

U.S. PATENT DOCUMENTS 5,872,808 A * 2/1999 Davidovici et al. ............ 375/152
6,122,295 A * 9/2000 Kato et al. ..................... 370/479
(Continued)

FOREIGN PATENT DOCUMENTS

EP     1830590 A2    9/2007
WO     0159936 A2    8/2001

OTHER PUBLICATIONS

International Search Report and Written Opinion of the International Searching Authority mailed Apr. 9, 2013.

*Primary Examiner* — Danh Le
(74) *Attorney, Agent, or Firm* — Duane Morris LLP (57) ABSTRACT

Apparatus and method for recognizing Global System for Mobile communication (GSM) signals are provided. The solution comprises obtaining position and timing information from a satellite positioning system; tuning to a frequency channel with GSM transmission; collecting a group of I/Q samples for the length of 12 GSM frames; performing peak detection using at least two peak detectors over the group of samples wherein the found peak values are the locations of synchronization bursts (SCH). For the found peaks, the timing information, carrier-to-noise ratio, in phase and quadrature values are determined. A group of I/Q samples for the length of 12 or 51 GSM frames are collected. From the found SCH, base station identification code BSIC, frame number and Broadcast Control Channel (BCCH) training sequence are determined. BCCHs corresponding to all SCH are decoded; and transmitting base stations identified.

19 Claims, 5 Drawing Sheets

(51) Int. Cl.
  *H04M 1/725* (2006.01)
  *H04B 7/212* (2006.01)

(56) References Cited

U.S. PATENT DOCUMENTS 6,256,486 B1    7/2001  Barany
6,563,856 B1 *  5/2003  O'Shea et al. ............... 375/130
2004/0142728 A1 *  7/2004  Tari et al. ...................... 455/561
2004/0266423 A1 * 12/2004  Morikawa et al. ............ 455/424
2005/0070241 A1 *  3/2005  Northcutt et al. ............. 455/265
2005/0180351 A1    8/2005  Peric
2009/0232125 A1 *  9/2009  Kim et al. ...................... 370/350
2010/0226264 A1 *  9/2010  Axmon et al. ................ 370/252
2012/0300755 A1 * 11/2012  Ancora et al. ................ 370/336

* cited by examiner

APPARATUS AND METHOD FOR DETECTING CO-CHANNELS SIGNALS

RELATED APPLICATIONS

This application is a U.S. national stage application of International Application No. PCT/FI2012/051262 entitled "Apparatus and Method for Detecting Co-Channels Signals", having an international filing date of 18 Dec. 2012, which claims priority to U.S. application Ser. No. 13/334,528 entitled "Apparatus and Method for Detecting Co-Channels Signals, filed 22 Dec. 2011, now U.S. Pat. No. 8,406,789. The entirety of each of the above-mentioned applications is hereby incorporated herein by reference.

FIELD

The exemplary and non-limiting embodiments of the invention relate generally to an apparatus and a method in wireless communication networks. Embodiments of the invention relate especially to detecting co-channel signals in wireless communication environment.

BACKGROUND

The following description of background art may include insights, discoveries, understandings or disclosures, or associations together with disclosures not known to the relevant art prior to the present invention but provided by the invention. Some of such contributions of the invention may be specifically pointed out below, whereas other such contributions of the invention will be apparent from their context.

Because frequency spectrum is a limited resource, several communication systems may share the same spectrum. In a given frequency spectrum a given number of frequency bands may be given to different operators or carriers in different locations. Typically each operator performs independent cellular coverage planning.

Present day methods for measuring cellular coverage in a cellular carrier's networks utilize radio scanners which operate in the cellular frequency bands. Typically, a route is driven using a vehicle equipped with the scanner equipment for collecting over-the-air downlink signals from the carrier's cell sites. GPS is used to geographically map the coverage area using specific signaling parameters for a given cellular technology. For Global System for Mobile communication (GSM) systems, signaling parameters measured and collected include received signal strength (RSSI), carrier-to-noise plus interference (CINR), the base station identifier code (BSIC), and broadcast channel (BCCH) messages. Within the BCCH messages are radio resource pseudo-length messages as specified in 3GPP standards. Within the set of BCCH messages include System Info Type 3 and 4 messages which provide information detailing the specific cell id, country code (MCC), network code (MNC), and location area code (LAC), among other information.

Present-day equipment offers the ability to show BSIC values and CINR values along with the GPS mapping of the carrier's coverage area which help reveal where there might be co-channel problems. Co-channel interference occurs when the frequency reuse plans are not optimized in a cellular network. In other words, two cell sites which cover the same region occupy the exact same radio frequency (the same absolute radio-frequency channel number, ARFCN). Typically a network is considered optimized if the CINR is maintained around 8-9 dB with RSSI levels down to −102 dB at which point a cellular phone would perform a hand-off to another stronger cell and is designed to operate.

However, present-day scanners do not provide simultaneous collection of more than one base station signal. Thus, both the desired and the interfering signals cannot be decoded simultaneously. Typically the only way of detecting possible co-channel interference is finding that the measured CINR is below the expected 8-9 dB with received signal strength above −102 dB. The existence and identification of co-channel interference is possible only when the collected data is post-processed in laboratory environment. This is tedious and slow.

SUMMARY

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to a more detailed description that is presented later.

According to an aspect of the present invention, there is provided an apparatus comprising at least one processor configured to cause the apparatus to: control a receiver to tune to a frequency channel with Global System for Mobile communication (GSM) transmission; control a receiver to collect a first group of in phase and quadrature (I/Q) samples; perform correlation on the first group of I and Q samples; perform peak detection using at least two peak detectors over the group of samples wherein the found peak values are the locations of synchronization bursts (SCH); for the found peaks, determine the timing information, carrier-to-noise ratio, in phase and quadrature values; control a receiver to collect a second group of in phase and quadrature (I/Q) samples; from the found SCH, determine identity information of the received transmission.

According to another aspect of the present invention, there is provided A method for recognizing Global System for Mobile communication (GSM) signals, the method comprising: tuning to a frequency channel with Global System for Mobile communication (GSM) transmission; collecting a first group of in phase and quadrature (I/Q) samples; performing correlation on the first group of I and Q samples; performing peak detection using at least two peak detectors over the group of samples wherein the found peak values are the locations of synchronization bursts (SCH); for the found peaks, determining the timing information, carrier-to-noise ratio, in phase and quadrature values; collecting a second group of in phase and quadrature (I/Q) samples; from the found SCH, determining identity information of the received transmission.

LIST OF DRAWINGS

Embodiments of the present invention are described below, by way of example only, with reference to the accompanying drawings, in which.

DESCRIPTION OF SOME EMBODIMENTS

Embodiments are applicable to any base station, user equipment (UE), server, corresponding component, and/or to any communication system or any combination of different communication systems that support required functionalities.

The protocols used, the specifications of communication systems, servers and user terminals, especially in wireless communication, develop rapidly. Such development may require extra changes to an embodiment. Therefore, all words and expressions should be interpreted broadly and they are intended to illustrate, not to restrict, embodiments.

Many different radio protocols to be used in communications systems exist. Some examples of different communication systems are the universal mobile telecommunications system (UMTS) radio access network (UTRAN or E-UTRAN), long term evolution (LTE, known also as E-UTRA), long term evolution advanced (LTE-A), Wireless Local Area Network (WLAN) based on IEEE 802.11 standard, worldwide interoperability for microwave access (WiMAX), personal communications services (PCS) and systems using ultra-wideband (UWB) technology. IEEE refers to the Institute of Electrical and Electronics Engineers.

Figure 1:
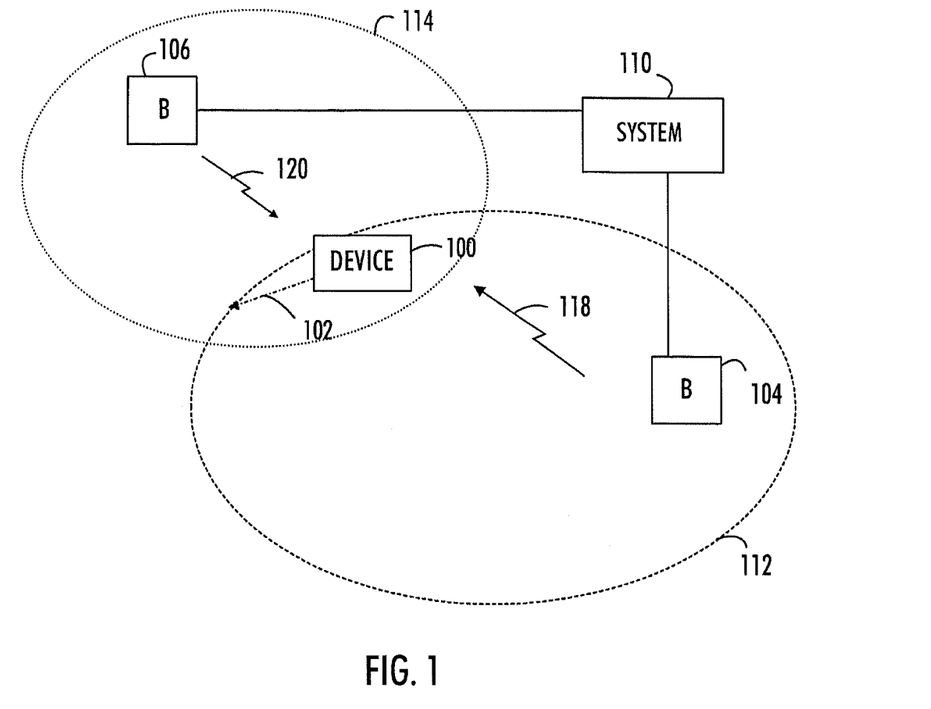
FIG. 1 illustrates an example of a communication environment.

FIG. 1 illustrates a simplified view of a communication environment only showing some elements and functional entities, all being logical units whose implementation may differ from what is shown. The connections shown in FIG. 1 are logical connections; the actual physical connections may be different. It is apparent to a person skilled in the art that the systems also comprise other functions and structures. It should be appreciated that the functions, structures, elements and the protocols used in or for communication are irrelevant to the actual invention. Therefore, they need not to be discussed in more detail here.

FIG. 1 shows an apparatus 100 traveling 102 in an area which is served by more than one two base stations 104, 106 of a communication system 110. The base stations have coverage areas 112, 114 where the transmissions of the base stations are well received.

The apparatus 100 configured to receive the transmissions of the base stations. In this particular example, the apparatus 100 is so situated that it may receive the transmission 118 from base station 104 and the transmission 120 from base station 106. It should be noted that embodiments of the invention are not limited to any particular number of base stations.

The apparatus may be a scanner configured to measure and analyze the cellular coverage of a network or a system. Let assume that in the example of FIG. 1 the apparatus is configured to measure the cellular coverage of system 110. The apparatus may also be user equipment configured by the system to perform measurements along with normal operation. The apparatus may be user equipment, mobile station, a fixed station, a portable or fixed communication apparatus, a measurement or analyzing device, a scanner or any other kind of device configured to receive transmissions from base stations of communication systems. The apparatus may be a standalone device or it may be connectable to other devices such as personal computers, analyzers or other devices.

In an embodiment, the apparatus 100 is a software defined radio SDR. In SDR, many components traditionally implemented with hardware are realized as software running in one or more processors.

In this example, the communication system 110 is a GSM based systems and the base stations 104, 106 GSM base stations In GSM based systems, the base stations transmit a base station identification code BSIC which identifies the base station. Transceivers wishing to communicate with base stations detect the BSIC of the base stations before initiating communication with the base stations. As already mentioned, each base station transmits broadcast channel (BCCH) messages. The BCCH messages are provide information detailing the specific cell id, country code (MCC), network code (MNC), and location area code (LAC), among other information.

In usual circumstances, the frequencies allocated to nearby base stations do not overlap. However, there may be situations when the cell planning of different network carrier operators is not optimal and nearby cells use the same frequency. In the example of FIG. 1 let us assume that both base stations 104, 106 transmit on the same frequency channel. Thus, when the apparatus 100 measures the cell coverage of base station 104 it may receive the transmission of base station 106 as co-channel interference.

The interfering base stations need not be geographically adjacent. If the frequency reuse plan of a network is not optimal the signal of a base station farther away may extend farther as originally intended and cause interference to the operation of another base station of the same network carrier.

As with most cellular communication systems, GSM transmission includes traffic channels and signaling channels. The signaling channels include the following:
   Broadcast Channels (BCH)
   Broadcast Control Channel (BCCH)
   Frequency Correction Channel (FCCH)
   Synchronization Channel (SCH)
   Cell Broadcast Channel (CBCH)
   Common Control Channels (CCCH)
   Paging Channel (PCH)
   Random Access Channel (RACH)
   Access Grant Channel (AGCH)
   Standalone Dedicated Control Channel (SDCCH)
   Associated Control Channel (ACCH)
   Fast Associated Control Channel (FACCH)
   Slow Associated Control Channel (SACCH)

When a conventional GSM transceiver or receiver, whether being user equipment or a scanner, is turned on or arrives to a new geographical area it is configured to search for Frequency Correction Channel FCCH transmitted by all base stations. When FCCH is found the transceiver knows where Synchronization Channel SCH is located. From SCH the transceiver gets BSIC, BCC and information needed to receive Broadcast Control Channel BCCH and identify the base station and connect to the base station if needed.

Figure 2:
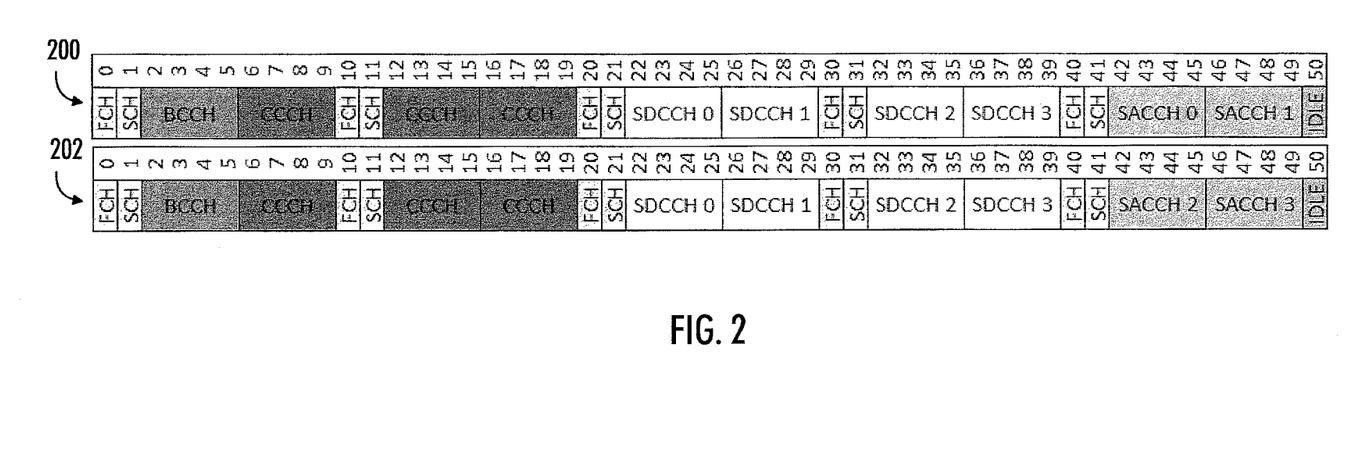
FIG. 2 illustrates an example of a GSM frame structure.

A typical GSM network signaling uses a repeating multi-frame sequence of two 51-frame multi-frames to include the SACCH channels. An example of this structure is illustrated in FIG. 2. Figure shows two successive multi-frames 200, 202 of a typical downlink channel in a GSM network. Here the repeating SCH bursts are to be noted as it is useful for the identification of co-channel signals. These bursts occur every 11 frames on the forward or downlink control channel. It should be noted that any periodic synchronization signaling within the 51 frame multi-frame could be used including the training sequences for normal bursts in addition to the extended training sequence in the SCH bursts. The advantage of the SCH bursts is the high repetition rate and the significance of 64 training sequence bits vs the 26 bits used for normal bursts.

The Slow Associated Control Channel SACCH that is associated with each Standalone Dedicated Control Channel SDCCH is only transmitted every other multi-frame. Each SACCH only gets half of the transmit time as the SDCCH that it is associated with. So, in one multi-frame, SACCH0 and SACCH1 would be transmitted, and in the next multi-frame, SACCH2 and SACCH3 would be transmitted.

Figure 3:
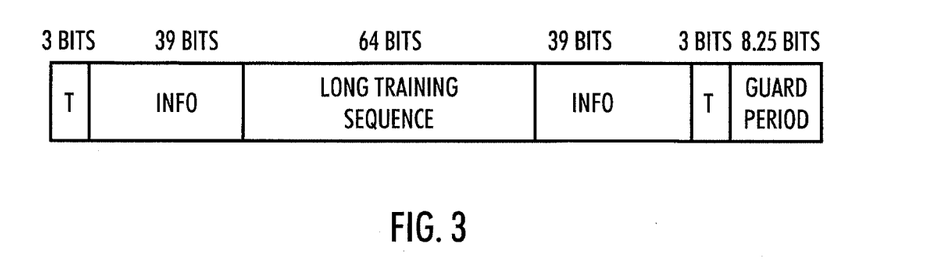
FIG. 3 illustrates the structure of the GSM synchronization burst

FIG. 3 illustrates the structure of the GSM synchronization burst SCH. The purpose of the SCH burst is to provide synchronization for the mobiles on the network. In the beginning of the burst are three tail bits which at the start of the GSM burst give time for a transmitter to ramp up its power. Then follow 39 bits of information, 64 bits of a Long or Extended Training Sequence and another 39 bits of Information. Finally, three 3 tail bits to enable the transmitter power to ramp down and 8.25 bits guard time to act as a guard interval.

A SCH burst contains a 64 bit extended training sequence which can provide a strong correlation gain even for weak signals. Typical GSM phones are designed to operate with a received signal having a signal level below −102 dBm. In a network the GSM performance should be capable of maintaining an 8 or 9 dB carrier-to-noise and interference (CINR) level for optimum performance to minimize bit errors. When two or more GSM signals operate on the same RF channel or ARFCN co-channel interference results. By using the SCH bursts as an indicator of co-channel signals the relative timing between the transmitters or time-difference-of-arrival (TDOA) of the signals and actual cell identification using BSIC decoding and/or broadcast channel (BCCH) decoding can identify the cells which are transmitting on the same frequency. Then the network operator, knowing the cells and GPS coordinates, can remedy the situation by changing the operating frequencies and/or the network frequency reuse plan. The network operator may utilize a movable scanner collecting and logging results in conjunction with GPS location(s) where the co-channel was detected.

Figure 4A:
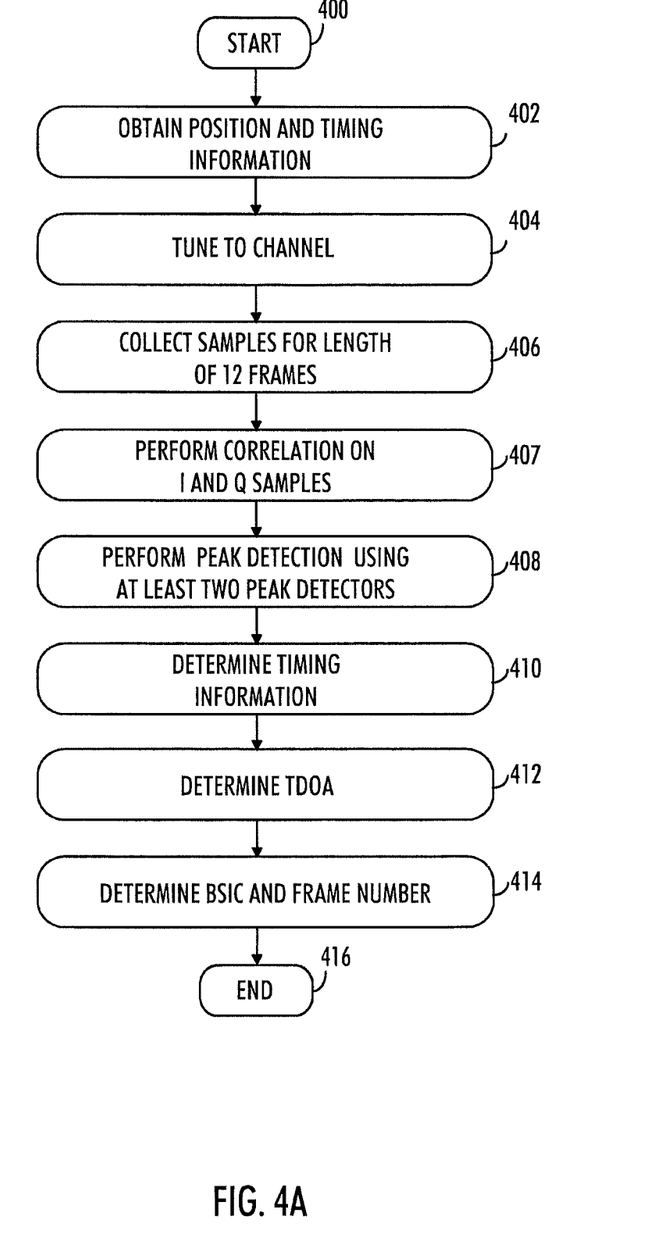
FIGS. 4A and 4B are flowcharts illustrating examples of embodiments of the invention.
Figure 4B:
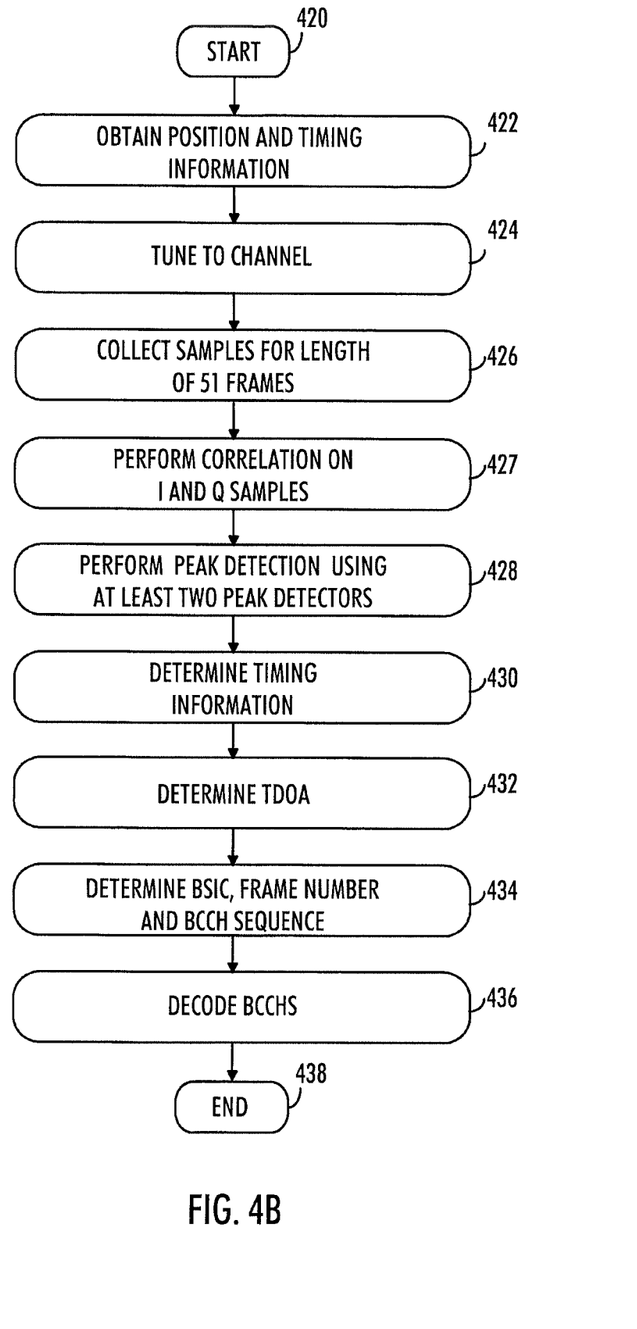

FIGS. 4A and 4B illustrate embodiments of the invention. The embodiments differ in the number of samples acquired. In the embodiment of FIG. 4A samples for the length of 12 GSM frames are collected whereas in the embodiment of FIG. 4B samples for the length of 51 GSM frames are collected. The selection whether to collect samples for the duration of length of 12 or 51 GSM frames is an implementation issue and depends upon application. If speed is of concern, the 12 frames may be collected. However, when 51 frames are collected it is guaranteed that the BCCH 4 frame bursts would be collected.

In the 12 frame configuration for collection the probability of collecting the BCCH 4 frame bursts is not as good as in the 51 frame configuration but the speed at which the process may be done is over four times faster. Thus, when 12 frames are collected BSIC decoding may be performed accurately. The selection of the frame configuration is used to help optimize scanning performance depending on whether one is interested in scanning a lot of channels (use the 12 frame configuration) or one is interested in scanning a few channels where the user could use the 51 frame configuration. The 51 frame configuration may be used to ensure the collect of the BCCH messages which are radio resource messages and specifically to be able to decode the System Info Type 3 and 4 messages which include cell identification information.

FIG. 4A is a flowchart illustrating an embodiment of the operation of the apparatus 100 of FIG. 1.

The embodiment starts at step 400.

In step 402, position and absolute timing information is obtained from a satellite positioning system. This may be done by controlling a GPS receiver to obtain required information. Absolute timing information means in this context the time kept by the GPS.

In step 404, the receiver or transceiver of the apparatus is tuned to a frequency channel with GSM transmission. Thus, the receiver or transceiver searches for FCCH signal transmitted by a base station and when found, tunes to the found channel. FCCH is used for the purpose of finding a channel because in GSM system it is specifically designed for this purpose.

In step 406, the receiver or transceiver of the apparatus collects a group of in phase and quadrature (I/Q) samples for the length of 12 GSM frames. In an embodiment, the receiver or transceiver performs GSM SCH matched filtering of I and Q signal paths over 12 complete GSM frame periods at a sample rate of 2× symbol rate resulting over 2500 samples.

In step 407, correlation is performed on the group of I and Q samples. In an embodiment, the correlation is performed using a field-programmable gate array (FPGA). In an embodiment, the correlation is implemented using 114 tap filter for each I and Q channel. At a double sample rate of the symbol rate for non-GMSK modulation 128 taps may be useful. For GSMK the modulation necessary to generate the I and Q coefficients renders some symbols ineffective due to the forward looking effect in GMSK modulation. In an embodiment, four forward looking symbols are used. Thus, out of 64 symbols the first three and the last three are not represented providing symbols 4-61 or 57 useful symbols.

For GMSK, each symbol is a composite of preceding symbols so the first three and the last three symbols of the 64 symbol long training sequence are indeterminant. The 114 tap length correlation then accounts for at best 57 of the 64 symbols. In an embodiment, the symbols at the front and at the end are skipped during the tap 114 I and Q channel correlation process.

In step 408, peak detection is performed using at least two peak detectors over the group of samples wherein the found peak values are the locations of synchronization bursts (SCH). In an embodiment, the apparatus performs peak detection of SCH matched filter normalized magnitude over collect of 12 frame sample data to encompass one complete transmittal of FCCH+SCH bursts repetition interval.

In a typical case two peak detectors are utilized. In such a case primary and one secondary or co-channel signal may be detected and recognized. This covers the majority of cases as it would be rare to have three nearby GSM base stations utilize the same frequency channel.

In step 410, for the found peaks, timing information, carrier-to-noise ratio and in phase and quadrature values are determined. In an embodiment, the determination of timing information comprises time stamping peak positions as an index offset relative to a GPS 1 PPS (1 Pulse per Second signal aligned to Coordinated Universal Time UTC) and to each other.

In an embodiment, parameters determined for each significant SCH burst peak detected include for example following:

The sample index relative to the start of the sample of collect may be determined and the sample index relative to GPS time offset from 1 sec. Normalized correlation peak or signal to noise ratio, $Es^2/Io^2(n)$, where n is the index of the sample with the peak value is calculated. In addition, normalized correlation peak one sample early, $Es^2/Io^2(n-1)$ and normalized correlation peak one sample later, $Es^2/Io^2(n+1)$ may be determined, where n is the index of the sample with the peak value is calculated. The Es2/Io2 values may be used to obtain a more refined timing estimate for timing adjustments in the demodulation and decoding of the SCH bursts. The three peak values at n, n−1, and n+1 may be used in a parabolic fit algorithm to estimate the fractional timing error based on the proportion of the correlation in the adjacent samples. A −0.5 to +0.5 timing adjustment can be made to locate the optimum fractional resampling point for demodulation and decoding.

Furthermore, in phase and quadrature (I and Q) values may be determined for samples of the correlation peaks, I and Q values at one sample later and at one sample early of correlation peaks and also $Io^2$, average of samples.

The computation of CINR using $Es^2/Io^2$ for both primary and secondary or co-channel signals provides valuable and useful information. The CINR noise floor with no co-channel should typically be around −6 dB. When a co-channel interference signal exists, the primary CINR may decrease below the preferred 8/9 dB.

An example of an equation which may be used to compute carrier-to-noise and interference (CINR) using the parabolic fitted $Es^2/Io^2$ value is:

$$CINR=10*\log(Es^2/(Io^2-Es^2)).$$

In step 412, the apparatus is configured to determine time-difference-of-arrival (TDOA) between the found peak values using the determined timing information. The apparatus may be configured to calculate the timing or time-difference-of-arrival (TDOA) between two dominant and significant peaks using the SCH burst correlation indexes.

In step 414, the apparatus is configured to, from the both dominant SCHs found, determine base station identification code BSIC.

The process ends in step 416.

FIG. 4B is a flowchart illustrating another embodiment of the operation of the apparatus 100 of FIG. 1.

The embodiment starts at step 420.

The step 422 is similar to the step 402 of FIG. 4A, i.e., position and absolute timing information is obtained from a satellite positioning system.

The step 424 is similar to the step 404 of FIG. 4A, i.e., the receiver or transceiver of the apparatus is tuned to a frequency channel with GSM transmission.

In step 426, the receiver or transceiver of the apparatus collects a group of in phase and quadrature (I/O) samples for the length of 51 GSM frames.

In step 427, correlation is performed on the group of I and Q samples in a similar manner as described in connection with step 407 above. In an embodiment, the correlation is performed using a field-programmable gate array (FPGA).

Figure 5:
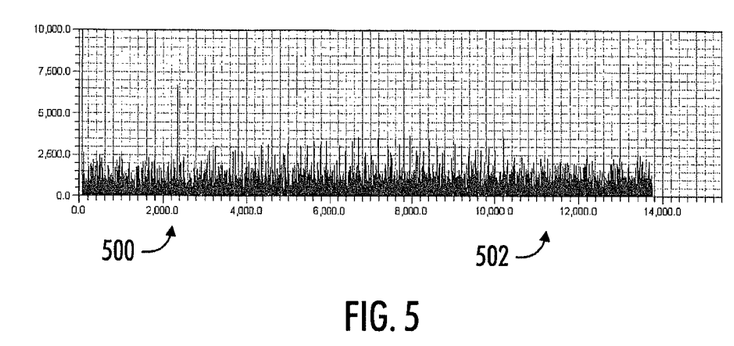
FIG. 5 illustrates an example of correlation results.

In step 428, peak detection is performed using at least two peak detectors over the group of samples. Further, in step 430, for the found peaks, timing information, carrier-to-noise ratio and in phase and quadrature values are determined. In processing the 51 frame collection of a GSM signal the SCH bursts of both primary and co-channel signals will be contained in the collect. This is due to the fact that all GSM downlink signaling will repeat at the 51 frame multi-frame sequence and the SCH bursts will repeat every 10 or 11 frames. The SCH matched filter/correlator will provide correlation peaks at the SCH burst locations of the two signals. FIG. 5 illustrates an example of correlation results with the primary and co-channel signal peaks. In this example, a first GSM signal is a few dB below the other GSM signal. In the example of FIG. 5, the correlation result for odd samples is illustrated, with the sample number on the x-axis and the correlation on y-axis. Here the two dominant peaks occur, one 500 just above the sample number 2000 and another 502 just below the sample number 12000.

By acquiring the sample indexes of the peak values the apparatus is agile and can quickly locate the SCH burst samples collected and decode the BSIC and/or the BCCH bursts if they also are contained in the collect. The BCCH bursts are included if the SCH burst either occurred sufficiently early in the collect or sufficiently later in the collect.

In step 432, the apparatus is configured to determine time-difference-of-arrival (TDOA) between the found peak values using the determined timing information.

In step 434, the apparatus is configured to, from the both dominant SCHs found, determine base station identification code BSIC, the number of the frame where the SCH is and Broadcast Control Channel (BCCH) training sequence for the found SCHs. On the basis of the frame number the apparatus is able to find the BCCH.

In step 436, the apparatus is configured to decode BCCHs corresponding to the found SCHs. The apparatus is configured to perform BCCH burst processing of both dominant SCH burst peaks to decode System Info Type 3 and 4 radio resource messages which include cell id and cell site information included in System Info Type 3 and 4.

In an embodiment, the apparatus is configured to associate decoded SCH and BCCH bursts with the received primary and co-channel signals to identify interfering cells.

The process ends in step 438.

Since separate cell sites are not necessarily frame aligned the SCH and BCCH bursts from one cell site most likely will occur in a different time position over the 10/11 GSM frame periods than the SCH and BCCH bursts from another cell site when both are transmitting on the same ARFCN.

The ability to GPS time stamp the peak locations is utilized in time-difference-of-arrival (TDOA) measurements. When the either the CINRs of the two interfering cells are too weak to decode any of the SCH or BCCH bursts without errors the synchronization signals (SCH bursts) will remain dominant and the CINRs and TDOAs will be valuable information for associating the two and tracking the interference patterns during a drive of the network.

When the BSICs and BCCH bursts can be decoded then the information can be completed to associate the cells exactly. In cases where the network operator knows the cell site database information the BSICs alone may be sufficient information. Also, the BCCH bursts being decoded and specifically the System Info Type 3 message contents can be used to exactly identify the cells in an operator's network.

In developing the present solution it was discovered that a good way to visualize the co-channel environment would be to identify and associate timing information with the occasional decodes of the GSM BSIC and/or BCCH of the signals. This way the two interfering GSM signals can be properly identified over time. When an interfering signal such as co-channel exists the direct signal as well as the co-channel signal may both be difficult to decode successfully without cyclic redundancy check (CRC) errors. At some point during a test drive both signals may be able to be successfully decoded due to the time varying propagation conditions. Although they may not both be successfully decoded at the same time the timing relationship can be associated when they are decoded.

A signal's frame number and timing is provided by the GSM frame number when a successful BSIC decode occurs with the addition of a timing index relative to GPS from the scanning hardware. The timing index is directly related to the GSM SCH burst within a GSM frame. When the signals can be decoded without CRC errors they can be tagged and associated with the timing information. The GSM SCH correlations present significant peaks which are used to establish timing indexes relative to GPS. If these are plotted over time the interference patterns will be clearly revealed. The GSM signal will most likely have CRC errors when co-channel is present. Although there are CRC errors the fact that the status shows CRC errors coupled with a CINR near 0 dB implies the presence of a significant SCH burst and decode attempt. The presence of multiple GSM SCH bursts will still provide timing indexes that can be plotted. Once the SCH burst can be decoded to extract the BSICs then the association to the timing information can be established. Over time both direct and co-channel signals will be decoded.

Whether a BSIC or BCCH decode is successful or not the SCH burst timing and TDOA may be provided along with the measured CINR. As described previously eventually successful decodes will occur. For GSM signals when there are significant CRC errors in the BSIC decoding operation there most likely exists co-channel interference, multipath interference, or weak signal conditions. Utilization of the time indexes and Es/Io (CINR) values for the two dominant peaks will reveal the presence of the interference. Eventually each of the two signals will be successfully decoded and reveal itself in terms of BSIC code, frame number, and BCCH information. The GPS mapping will also provide the operator locations of specific interference problems.

Figure 6:
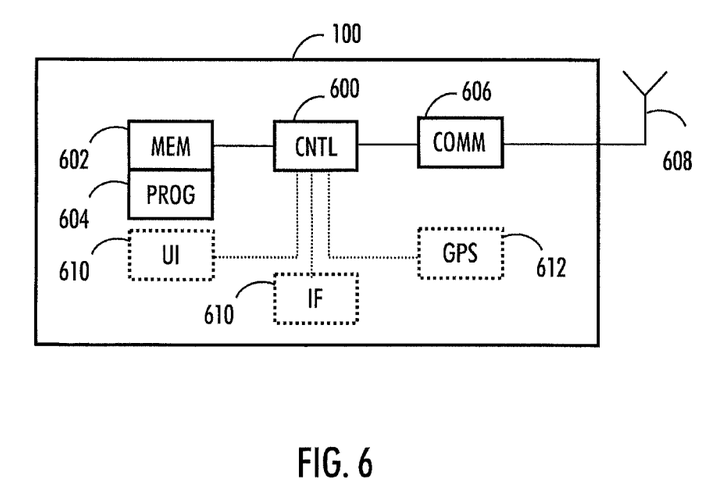
FIG. 6 illustrates an example of an apparatus.

FIG. 6 illustrates an embodiment. The figure illustrates a simplified example of an apparatus 100 applying embodiments of the invention. In some embodiments, the apparatus may be user equipment of a communications system. The apparatus may further be a measurement or analyzing device, a scanner or any other kind of device configured to receive transmissions from base stations or other elements of communication systems. The apparatus may be a standalone device or it may be connectable to other devices such as personal computers, analyzers or other devices.

The apparatus may also be interpreted as a circuitry implementing the required functionality within user equipment of a communications system or a measuring or analyzing device.

It should be understood that the apparatus is depicted herein as an example illustrating some embodiments. It is apparent to a person skilled in the art that the apparatus may also comprise other functions and/or structures and not all described functions and structures are required. Although the apparatus has been depicted as one entity, different modules and memory may be implemented in one or more physical or logical entities.

The apparatus of the example includes a control circuitry 600 configured to control at least part of the operation of the apparatus.

The apparatus may comprise a memory 602 for storing data. Furthermore the memory may store software 604 executable by the control circuitry 600. The memory may be integrated in the control circuitry.

The apparatus comprises a transceiver 606. The transceiver is operationally connected to the control circuitry 600. It may be connected to an antenna arrangement 608.

The software 604 may comprise a computer program comprising program code means adapted to cause the control circuitry 600 of the apparatus to control the apparatus to control a satellite positioning system receiver to obtain position and timing information from a satellite positioning system; control a receiver to tune to a frequency channel with Global System for Mobile communication (GSM) transmission; control a receiver to collect a group of in phase and quadrature (I/Q) samples for the length of 12 GSM frames; perform peak detection using at least two peak detectors over the group of samples wherein the found peak values are the locations of synchronization bursts (SCH); for the found peaks, determine the timing information, carrier-to-noise ratio, in phase and quadrature values; control a receiver to collect a group of in phase and quadrature (I/Q) samples for the length of 12 or 51 GSM frames; from the found SCH, determine base station identification code BSIC, frame number and Broadcast Control Channel (BCCH) training sequence for all SCH; decode BCCHs corresponding to all SCH; and determine time-difference-of-arrival (TDOA) between the found peak values using the determined timing information.

The apparatus may further comprise interface circuitry 610 configured to connect the apparatus to other devices and network elements of communication system The interface may provide a wired or wireless connection to personal computers, analyzers or other devices.

The apparatus may further comprise user interface 610 operationally connected to the control circuitry 600. The user interface may comprise a display, a keyboard or keypad, a microphone and a speaker, for example.

The apparatus may further comprise a satellite positioning receiver 612 such as a Global Positioning System (GPS) receiver operationally connected to the control circuitry 600.

In an embodiment, a matched filter used to detect SCH is implemented in a field-programmable gate array (FPGA) and operates on both the in phase and quadrature samples at a double sample rate or 270833 samples/sec×2. Higher sample rate filters are feasible for higher number of samples per symbol. In this implementation two samples per symbol were used.

The FPGA may also comprise two peak detectors, a primary and a secondary detector, which operate in tandem to minimize duplication of obtaining the same peaks.

In an embodiment, a traditional peak detector which operates over the 12 frames of the collected data may be used. The second peak detector is slaved to the first peak detector with limitations to prevent capturing the same peaks.

When the primary peak detector updates the secondary peak detector is disabled. The transfer of the primary peak to the secondary peak detector can occur only if not outside a window of the previous primary peak index. Also, the secondary peak update will not update when a peak is detected within a few samples of the primary index+10 frames. This will prevent capture of the same repeating SCH burst peak.

The steps and related functions described in the above and attached figures are in no absolute chronological order, and some of the steps may be performed simultaneously or in an order differing from the given one. Other functions can also be executed between the steps or within the steps. Some of the steps can also be left out or replaced with a corresponding step.

The apparatuses or controllers able to perform the above-described steps may be implemented as an electronic digital computer, which may comprise a working memory (RAM), a central processing unit (CPU), and a system clock. The CPU may comprise a set of registers, an arithmetic logic unit, and a controller. The controller is controlled by a sequence of program instructions transferred to the CPU from the RAM. The controller may contain a number of microinstructions for basic operations. The implementation of microinstructions may vary depending on the CPU design. The program instructions may be coded by a programming language, which may be a high-level programming language, such as C, Java, etc., or a low-level programming language, such as a machine language, or an assembler. The electronic digital computer may also have an operating system, which may provide system services to a computer program written with the program instructions.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

An embodiment provides a computer program embodied on a distribution medium, comprising program instructions which, when loaded into an electronic apparatus, are configured to control the apparatus to execute the embodiments described above.

The computer program may be in source code form, object code form, or in some intermediate form, and it may be stored in some sort of carrier, which may be any entity or device capable of carrying the program. Such carriers include a record medium, computer memory, read-only memory, and a software distribution package, for example. Depending on the processing power needed, the computer program may be executed in a single electronic digital computer or it may be distributed amongst a number of computers.

The apparatus may also be implemented as one or more integrated circuits, such as application-specific integrated circuits ASIC. Other hardware embodiments are also feasible, such as a circuit built of separate logic components. A hybrid of these different implementations is also feasible. When selecting the method of implementation, a person skilled in the art will consider the requirements set for the size and power consumption of the apparatus, the necessary processing capacity, production costs, and production volumes, for example.

In an embodiment, an apparatus comprises means for obtaining position and timing information from a satellite positioning system; means for tuning to a frequency channel with GSM transmission; means for collecting a group of in phase and quadrature samples for the length of 12 GSM frames; means for performing peak detection using at least two peak detectors over the group of samples wherein the found peak values are the locations of synchronization bursts SCH; means for, determining the timing information, carrier-to-noise ratio, in phase and quadrature values for the found peaks; means for collecting a group of in phase and quadrature samples for the length of 12 or 51 GSM frames; means for determining from the found SCH base station identification code BSIC, frame number and BCCH training sequence for all SCH; means for decoding BCCHs corresponding to all SCH; and means for determining time-difference-of-arrival between the found peak values using the determined timing information.

It will be obvious to a person skilled in the art that, as technology advances, the inventive concept can be implemented in various ways. The invention and its embodiments are not limited to the examples described above but may vary within the scope of the claim.

The invention claimed is:

1. An apparatus comprising at least one processor configured to cause the apparatus to:
   control a receiver to tune to a frequency channel with Global System for Mobile communication (GSM) transmission;
   control a receiver to collect a first group of in phase and quadrature (I/Q) samples;
   perform correlation on the first group of I and Q samples;
   perform peak detection using at least two peak detectors over the group of samples wherein the found peak values are the locations of synchronization bursts (SCH);
   for the found peaks, determine the timing information, carrier-to-noise ratio, in phase and quadrature values;
   control a receiver to collect a second group of in phase and quadrature (I/Q) samples; and
   from the found SCH, determine identity information of the received transmission.

2. The apparatus of claim 1, wherein the at least one processor further configured to:
   control a satellite positioning system receiver to obtain position and timing information from a satellite positioning system;
   determine from the found SCH base station identification code BSIC, frame number and Broadcast Control Channel (BCCH) training sequence for all SCH;
   decode BCCHs corresponding to all SCH; and
   determine time-difference-of-arrival (TDOA) between the found peak values using the determined timing information.

3. The apparatus of claim 2, wherein the at least one processor further configured to determine timing information of the found peaks utilizing information obtained from the satellite positioning system.

4. The apparatus of claim 3, the apparatus being configured to determine timing information of found peaks, the information comprising sample index relative to the start of collecting and sample index relative to satellite positioning system timing information.

5. The apparatus of claim 2, the apparatus being configured to determine carrier-to-noise ratios and in phase and quadrature values for samples corresponding to the peak value and one sample early and one sample later the peak value.

6. The apparatus of claim 2, the apparatus being configured to determine cell identification and cell site information from BCCHs corresponding to all SCH.

7. The apparatus of claim 5, the apparatus being configured to utilize the carrier-to-noise ratio information determined from samples corresponding to the peak value and one sample early and one sample later the peak value in determining timing information of found peaks.

8. The apparatus of claim 1, the apparatus being configured to determine average phase angle error value for synchronization bursts utilizing the in phase and quadrature value information determined from samples corresponding to the peak value and one sample early and one sample later the peak value.

9. The apparatus of claim 2, the apparatus being configured to associate decoded SCH and BCCH bursts with the received signals to identify interfering cells.

10. A method for recognizing Global System for Mobile communication (GSM) signals, the method comprising:
    tuning to a frequency channel with Global System for Mobile communication (GSM) transmission;
    collecting a first group of in phase and quadrature (I/Q) samples;
    performing correlation on the first group of I and Q samples;
    performing peak detection using at least two peak detectors over the group of samples wherein the found peak values are the locations of synchronization bursts (SCH);
    for the found peaks, determining the timing information, carrier-to-noise ratio, in phase and quadrature values;

collecting a second group of in phase and quadrature (I/Q) samples; and from the found SCH, determining identity information of the received transmission.

11. The method of claim 10, further comprising:

obtaining position and timing information from a satellite positioning system; from the found SCH, determining base station identification code BSIC, frame number and Broadcast Control Channel (BCCH) training sequence for all SCH;

decoding BCCHs corresponding to all SCH; and determining time-difference-of-arrival (TDOA) between the found peak values using the determined timing information.

12. The method of claim 11, further comprising:

determining timing information of the found peaks utilizing information obtained from the satellite positioning system.

13. The method of claim 12, further comprising:

determining timing information of found peaks, the information comprising sample index relative to the start of collecting and sample index relative to satellite positioning system timing information.

14. The method of claim 11, further comprising:

determining carrier-to-noise ratios and in phase and quadrature values for samples corresponding to the peak value and one sample early and one sample later the peak value.

15. The method of claim 11, further comprising:

determining cell identification and cell site information from BCCHs corresponding to all SCH.

16. The method of claim 14, further comprising:

utilizing the carrier-to-noise ratio information determined from samples corresponding to the peak value and one sample early and one sample later the peak value in determining timing information of found peaks.

17. The method of claim 11, further comprising:

determining average phase angle error value for synchronization bursts utilizing the in phase and quadrature value information determined from samples corresponding to the peak value and one sample early and one sample later the peak value.

18. The method of claim 11, further comprising:

associating decoded SCH and BCCH bursts with the received signals to identify interfering cells.

19. A non-transitory computer program product embodied on a distribution medium readable by a computer and comprising program instructions which, when loaded into an apparatus, execute a computer process comprising:

controlling a receiver to tune to a frequency channel with Global System for Mobile communication (GSM) transmission;

controlling a receiver to collect a first group of in phase and quadrature (I/Q) samples;

performing correlation on the first group of I and Q samples;

performing peak detection using at least two peak detectors over the group of samples wherein the found peak values are the locations of synchronization bursts (SCH);

for the found peaks, determining the timing information, carrier-to-noise ratio, in phase and quadrature values;

controlling a receiver to collect a second group of in phase and quadrature (I/Q) samples; and from the found SCH, determining identity information of the received transmission.

\* \* \* \* \*